United States Patent [19]
Dahlbäck et al.

[11] Patent Number: 5,887,586
[45] Date of Patent: Mar. 30, 1999

[54] METHOD AND SYSTEM FOR MEASURING A DOSE OF DRUG INHALED

[75] Inventors: Magnus Dahlbäck, Lund; Per-Olof Fagerström, Bjärred; Hans Marchner, Mariefred; Ola Nerbrink, Lund, all of Sweden

[73] Assignee: Astra Aktiebolag, Sodertalje, Sweden

[21] Appl. No.: 525,535

[22] PCT Filed: May 24, 1995

[86] PCT No.: PCT/SE95/00590

§ 371 Date: Sep. 15, 1995

§ 102(e) Date: Sep. 15, 1995

[87] PCT Pub. No.: WO96/00046

PCT Pub. Date: Jan. 4, 1996

[30] Foreign Application Priority Data

Jun. 23, 1994 [SE] Sweden .................................. 9402237

[51] Int. Cl.[6] ............................. A61M 16/10; A62B 7/00; F16K 31/02; A61B 5/08
[52] U.S. Cl. ................................ 128/204.22; 128/203.12; 128/203.15; 600/529; 600/532
[58] Field of Search ......................... 128/203.12, 203.14, 128/203.15, 204.22, 204.21, 204.26, 204.23, 716, 719, 724, 725; 600/529, 532

[56] References Cited

U.S. PATENT DOCUMENTS

| | | | |
|---|---|---|---|
| 3,498,294 | 3/1970 | Zeff et al. | 128/203.14 |
| 3,524,463 | 8/1970 | Rose et al. | 128/203.14 |
| 4,479,493 | 10/1984 | Bung et al. | 128/204.18 |
| 4,938,212 | 7/1990 | Snook et al. | 128/205.24 |
| 5,156,776 | 10/1992 | Loedding et al. | 128/203.12 |
| 5,313,955 | 5/1994 | Rodder | 128/204.21 |
| 5,347,999 | 9/1994 | Poss et al. | 128/203.15 |
| 5,487,378 | 1/1996 | Robertson et al. | 128/200.16 |
| 5,628,307 | 5/1997 | Clark et al. | 128/203.15 |

FOREIGN PATENT DOCUMENTS

| | | |
|---|---|---|
| 121795 A2 | 10/1984 | European Pat. Off. . |
| 2341924 | 3/1975 | Germany . |
| WO 96/00046 | 4/1996 | WIPO . |

Primary Examiner—Kimberly L. Asher
Attorney, Agent, or Firm—Fish & Richardson P.C.

[57] ABSTRACT

In a method for measuring a dose of a drug inhaled by an animal, the momentary concentration of the drug in an aerosol supplied to the animal and the momentary inhalation flow rate of the animal are determined. An inhaled partial dose is calculated from each determined inhalation flow rate value and a corresponding concentration value. The calculated inhaled partial doses are added to obtain the total dose inhaled by the animal.

8 Claims, 2 Drawing Sheets

METHOD AND SYSTEM FOR MEASURING A DOSE OF DRUG INHALED

This application is a 371 of PCT/SE95/00590 filed May 24, 1995.

BACKGROUND OF THE INVENTION

The present invention relates to a method for measuring a dose of a drug in aerosol form inhaled by an animal as well as a system for implementing the measuring method. The present invention also relates to a method for administering a predetermined dose of a drug in aerosol form to an animal and a system for implementing the administering method.

When performing animal experiments for testing a new drug, it is often desirable to administer a predetermined dose of the drug to each animal.

A method known in the art for administering a dose of a drug inhaled by an experimental animal in aerosol form is the fixed time administration method. The experimental set-up of this method is schematically shown in FIG. 1. An aerosol generator 1 is connected to one end of a tube 2, the other end of which is connected to a nose mask 3, through which the animal is to inhale during the experiment. The tube 2 is provided with an air inlet 4, comprising a one-way flap valve 5 and a filter 6, as well as an air outlet 7, also comprising a one-way flap valve 8 and a filter 9.

In a preparatory phase of the method, the exposure time required for administering a desired dose of the drug is calculated from the following relation Exposure time=desired dose×BW/(aerosol concentration×respiratory minute volume)

where BW is the body weight of the animal, the aerosol concentration is a predetermined particle concentration in the flow of aerosol generated by the aerosol generator, and the respiratory minute volume is calculated in a predetermined way according to a theory or empirical knowledge. Then, the aerosol generator 1 is adjusted so as to generate, in the tube 2, a fixed volumetric flow of aerosol of the predetermined concentration.

In the measurement phase, the animal inhales the aerosol through the nose mask 3 during the predetermined exposure time. If the animal needs more air than what is provided by the aerosol generator 1, additional air is supplied through the air inlet 4. Exhaled air and any air not inhaled by the animal leaves the system through the air outlet 7. The filters 6, 9 prevent contamination of the air outside the system.

However, it has been found that this prior-art fixed time administration method is not sufficiently accurate for use in certain experiments where the doses actually delivered must be in keeping with the planned doses.

SUMMARY OF THE INVENTION

Thus, a first object of the present invention is to provide a more accurate method and system for measuring the dose of a drug inhaled by an experimental animal in aerosol form.

A second object of the present invention is to provide a more accurate method and system for administering a predetermined dose of a drug in aerosol form to an experimental animal.

These objects are achieved by methods and systems having the features recited in the appended claims.

BRIEF DESCRIPTION OF THE DRAWINGS

One embodiment of the present invention will now be described in more detail with reference to the accompanying drawings, in which FIG. 1, which already has been discussed, is a schematic view of a prior-art experimental set-up for carrying out the fixed time administration method.

DESCRIPTION OF THE PREFERRED EMBODIMENTS

Figure 2:
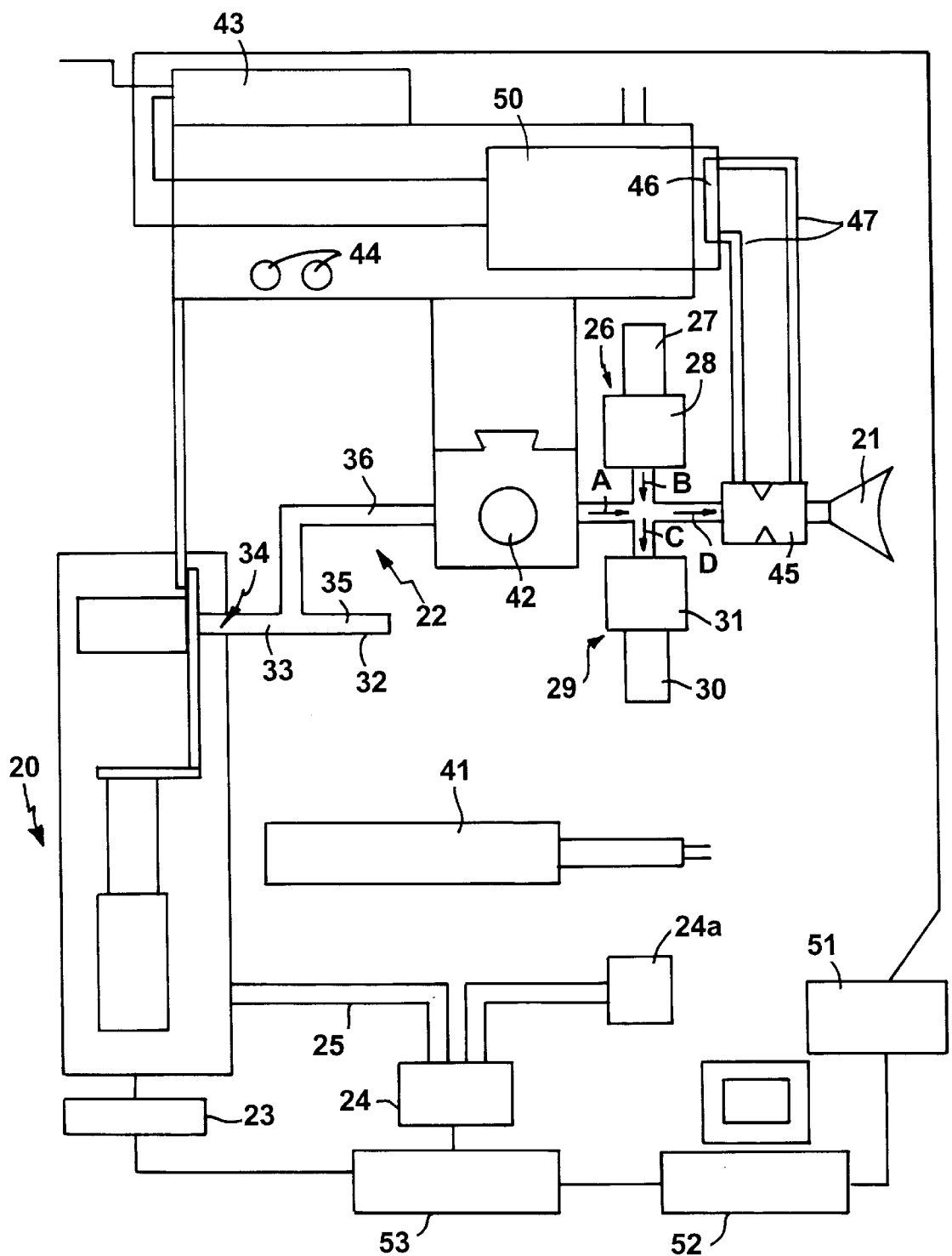
FIG. 2 is a block diagram of a system for administering a dose of a drug in the form of a dry-powder aerosol to an experimental animal and measuring the size of the dose.

The system shown in FIG. 2 for administering a dose of an aerosol essentially consists of an administration section and a measurement section.

Figure 1:
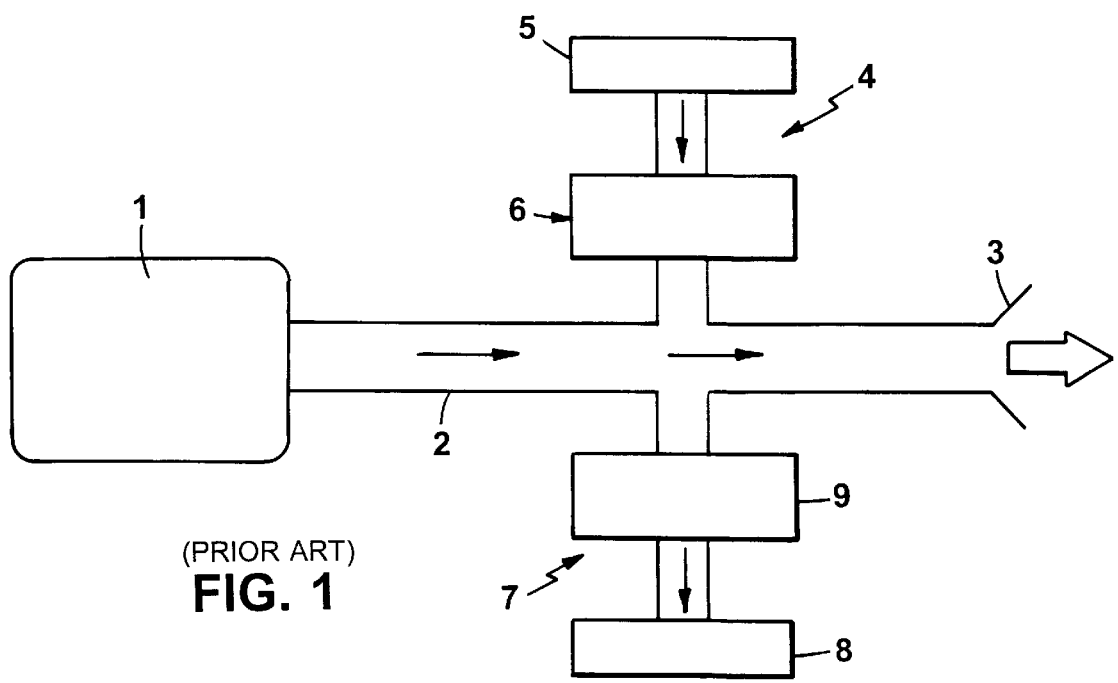

The administration section, which is similar to the system shown in FIG. 1, comprises a dry-powder aerosol generator 20, which is connected to a removable nose mask 21 via a conduit system 22.

The aerosol generator 20, which is a modified Wright Dust Feeder from Adams Ltd., London, Great Britain, comprises a scraping mechanism, by means of which powder can be scraped off a tablet of compressed powder, as well as means for aerosolising the scraped-off powder in an air flow. The scraping speed, and thus the concentration of the generated dry-powder aerosol, is controlled by an aerosol generator control unit 23, for instance a Motomatic II from Electro-Craft, South Eden Prairie, Minn.

The air flow used for aerosolising is controlled by a mass flow controller 24, which is connected to the aerosol generator 20 through a tube 25 and to which air is supplied from a source of pressurised air 24a.

The conduit system 22 comprises an air inlet 26 having a one-way flap valve 27 and a filter 28, as well as an air outlet 29 also having a one-way flap valve 30 and a filter 31. The conduit system 22 is further provided with a particle trap 32, consisting of a three-way connection, of which a first branch 33 is connected to the aerosol outlet 34 of the aerosol generator, a second branch 35 terminates in a dead end in which larger particles are trapped, and a third branch 36 leads to the nose mask 21.

In the following, four different air flows are discussed. 1) The air flow A from the aerosol generator to the junction of the air inlet 26 and the air outlet 29. This air flow contains aerosolised particles and is, accordingly, referred to as a flow of aerosol. 2) The air flow B through the air inlet 26. 3) The air flow C through the air outlet 29. 4) The air flow D from the junction of the air inlet 26 and the air outlet 29 towards the animal. This air flow is the air flow inhaled by the animal and is, accordingly, referred to as the inhalation flow. The inhalation flow D equals the flow of aerosol A plus the air flow B (if any) minus the air flow C (if any).

The measurement section of the system essentially consists of means 41, 43, 50 for determining the particle concentration of the aerosol flow A, means 45, 46, 50 for determining the inhalation flow rate, and a computer 52.

The means 41, 43, 50, for determining the particle concentration comprises a light-scattering instrument 41, 43, for instance a Casella AMS 950 from Casella Ltd., London, Great Britain. The instrument has a measuring probe 41, which is shown separately in FIG. 2, but which is placed in a probe holder 42 when the system is used, and a display section 43 for displaying the measured particle concentrations.

The probe holder 42 and the measuring probe 41 are inserted in the conduit system 22 in such a way that the flow of aerosol A from the aerosol generator 20 passes through the measuring probe 41 on its way to the nose mask 21.

To prevent contamination of the lenses of the measuring probe 41, air is supplied to the measuring probe 41 through two plastic tubes (only the air outlets 44, to which the tubes are to be connected, are shown in FIG. 2).

The means 45, 46, 50, for determining the inhalation flow rate comprises an air flowmeter having an air flow restriction 45 and a pressure transducer 46 for measuring the air pressure difference over the flow restriction. The air flow restriction 45 is connected to the pressure transducer 46 through two tubes 47.

The air flowmeter 45, 46 and the light-scattering instrument 41, 43 are connected to a processing unit 50, which, via an interface 51, is connected to the computer 52, for instance a PC, which in turn is connected to a control unit 53 for controlling the operation of the mass flow controller 24 and the control unit 23 of the aerosol generator.

The light-scattering instrument does not always measure the absolute particle concentration. The instrument also depends on the physical characteristics of the aerosol. Thus, the instrument has to be calibrated. Furthermore, the particle concentration of the aerosol flow A at the junction of the air inlet 26 and the air outlet 29 is lower than the particle concentration of the aerosol flow A measured by the light-scattering instrument 41, 43, because some particles get caught in the conduits on their way to the nose mask 21. Thus, to establish the absolute particle concentration of the aerosol flow A at the junction of the air inlet 26 and the air outlet 29, the output signal from the light-scattering instrument has to be modified by a correlation factor.

To determine the correlation factor, the flap valves 27, 30 are plugged, and a test filter is inserted in the part of the conduit extending between, on the one hand, the nose mask 21 and, on the other hand, the junction of the air inlet 26 and the air outlet 29. The aerosol generator 20 is adjusted so as to generate an aerosol flow A having a predetermined particle concentration and a predetermined volumetric flow rate. The system is operated during a predetermined time period. Then, the mass of particles on the test filter is determined, and the correlation factor is calculated from the ratio of the total particle concentration measured by the light-scattering instrument, to the corresponding particle concentration determined by means of the mass of particles on the test filter.

When the instrument is used to determine the concentration of the active substance in the aerosol, only the active substance on the filter is determined and taken into account when calculating the correlation factor.

When the correlation factor has been determined, the flap valves 27, 30 are unplugged and the test filter is removed.

The operation of the system according to the present invention will now be described.

When performing an experiment in which a predetermined dose of an aerosol is to be administered to an experimental animal, the value of the predetermined dose is first entered in the computer 52, and a maximal test duration, long enough for the predetermined dose to be achieved, is set. Other data needed for the experiment may also be entered, for instance information about the experimental animal and the drug. Then, the scraping rate of the aerosol generator 20 is adjusted so that the predetermined dose is assumed to be administered during a desired time period. The nose mask 21 is fastened on the experimental animal, for instance a dog, and the system is started.

The aerosol generator 20 is adjusted so as to continuously generate a flow of aerosol A of a predetermined volumetric flow rate and a predetermined aerosol particle concentration. In practice, however, the aerosol particle concentration often varies considerably during an experiment.

The flow of aerosol A is output from the aerosol outlet 34 into the conduit system 22. Large particles in the aerosol are trapped in the particle trap 32.

As mentioned above, air is supplied to the measuring probe 41 of the light-scattering instrument 40 to prevent contamination of its lenses. This flow of air, which has a predetermined volumetric flow rate, is added to the flow of aerosol A from the aerosol generator 20.

The measuring probe 41 measures the light scattered by the particles in the flow of aerosol A. The measured values are supplied to the processing unit 50.

Furthermore, the pressure transducer 46 measures the pressure difference across the air flow restriction 45, and supplies the pressure difference values to the processing unit 50.

The pressure difference across the air flow restriction 45 is measured at a frequency of at least 50 Hz, since the inhalation flow rate varies considerably during an inhalation made by the animal. The particle concentration is preferably measured at the same frequency, but it may also be measured much more seldom since the concentration varies much more slowly.

The processing unit 50 successively calculates the particle concentrations corresponding to the sampled light values, as well as the air flow rates corresponding to the sampled pressure difference values caused by the inhalations by the animal. The calculated values are forwarded to the computer 52, which calculates an inhaled partial dose for each determined inhalation flow rate value by multiplying the determined inhalation flow rate value by the corresponding determined particle concentration and the time elapsing between two successive determinations of the inhalation flow rate.

If the particle concentration is determined at a lower frequency than the inhalation flow rate, the last determined particle concentration may be used for the calculation of the inhaled partial doses.

The partial inhaled doses may be calculated in real time, or during the exhalations by the animal, or even after the termination of the experiment.

The experimental animal sometimes inhales more air than what is supplied from the aerosol generator 20, at least during the peak of the inhalation. The additional air needed is supplied through the air inlet 26. It results in a reduction of the particle concentration of the inhalation flow D. Thus, the particle concentration measured by the light scattering instrument 41, 43 does not reflect the particle concentration of the inhalation flow D.

This problem is solved in the following manner. When additional air B is supplied through the air inlet 26, an inhalation flow rate exceeding the predetermined flow rate of the flow of aerosol A from the light-scattering instrument will be detected when measuring over the flow restriction 45. In this case the computer 52 uses the predetermined flow rate instead of the inhalation flow rate measured across the air flow restriction 45 for the calculation of the inhaled partial dose because the additional air B from the air inlet 26 does not increase the dose inhaled by the animal.

The computer 52 cumulates the inhaled partial doses by adding each calculated inhaled partial dose to a sum of all previously calculated inhaled partial doses. After each inhaled partial dose added, this cumulated dose is compared with the predetermined dose. When the predetermined dose is achieved, or when the maximal test duration has expired, the computer 52 outputs a signal to the control unit 53 to stop the aerosol generator 20. The experimental animal is allowed to make a few more inhalations to prevent any remaining aerosol from leaking out.

The part of the conduit system 22 extending between the nose mask 21 and the flow restriction 45 will not contain any aerosol when the animal begins its inhalation, which means that the actual dose inhaled by an animal during an inhalation is less than the dose calculated by means of the inhalation flow rate values and concentration values.

For this reason, the inhaled dose calculated for each inhalation (each tidal volume) is advantageously corrected for this "dead space" between the nose mask 21 and the flow restriction 45, by means of the equation (TV-DV)/TV, where TV is the tidal volume, determined by means of the measured inhalation flow rate value, and DV is the volume of the dead space.

EXAMPLE

An experiment was carried out to compare the prior art fixed time administration method (method 1) with the method according to the present invention (method 2) as regards the ability to predict the dose of an aerosol inhaled by an animal.

The system illustrated in FIG. 2 was used with a test filter inserted between the flow restriction 45 and the nose mask 21. The test substance was budesonide.

The experiment was performed on five dogs at three different target concentrations, 60 $\mu$g/l, 200 $\mu$g/l and 1500 $\mu$g/l. Four trials were performed at each concentration with each dog.

The exposure time was allowed to vary from 3.5 to 5 minutes. The substance correlation factors used were 0.4570, 0.4709 and 0.5075 for the target concentrations 60 $\mu$g/l, 200 $\mu$g/l and 1500 $\mu$g/l, respectively.

The ratio of the mass of test substance on the test filter to the mass of test substance predicted by methods 1 and 2 was calculated and analysed by analysis of variance. The 95% confidence intervals and the standard deviations of the two methods were computed. As appears from the following table, the best prediction of the inhaled dose was obtained by the method according to the present invention when corrected for the dead space.

| Method | Remark | Mean | 95% Conf.limit | 95% Conf.limit | Standard Deviation |
| --- | --- | --- | --- | --- | --- |
| Fixed time administration | | 1.77 | 1.70 | 1.84 | 0.27 |
| The invention | Uncorr. dead space | 0.86 | 0.85 | 0.88 | 0.06 |
| | Corr. dead space | 0.94 | 0.93 | 0.96 | 0.07 |

The embodiment described above is but an example which may be modified in many ways within the scope of the appended claims.

The particle concentration of the flow of aerosol may be measured by any suitable non-intrusive technique, for instance by means of ultrasonic sound. Furthermore, the mass flow rate of the aerosol flow may be measured instead of the volumetric flow rate.

Provided that the flow rate of the aerosol flow A is known or is measured, the air flowmeter 45, 46 measuring the flow rate of the inhalation flow may be replaced by an air flowmeter measuring the air flow rate in the air outlet 29. Optionally, the system may also be provided with an air flowmeter measuring the air flow rate in the air inlet 26.

The flap valve 30 and the filter 31 of the air outlet 29 may be replaced by a recirculation conduit leading back to the conduit system 22 upstream of the means 41, 43, 50 in order to reuse active substance exhaled or not inhaled by the test animal.

In the embodiment described above, the particle concentration is measured upstream from the air inlet 26, and the air outlet 29. However, it may also be measured downstream thereform.

In addition to dry-powder aerosol, the systems and the methods according to the invention may be used for liquid aerosols and aerosols obtained from pressurised metered dose inhalers.

The methods and the systems according to the invention are to be used when performing experiments on animals, preferably large animals, for instance dogs and pigs, but also smaller animals like rats and rabbits.

We claim:

1. A method for measuring a dose of a drug inhaled by an experimental animal, the drug being supplied to the animal in the form of a flow of aerosol, characterised by the steps of (a) determining the momentary concentration of the drug in said flow of aerosol;

(b) determining the momentary inhalation flow rate of the animal a plurality of times during each inhalation by the animal;

(c) calculating an inhaled partial dose for each determined momentary flow rate;

the total dose of the drug inhaled by the animal being obtained by summation of all inhaled partial doses, wherein the aerosol flow rate at the point where the momentary concentration of the drug is determined, is known or is determined, characterised in that the calculation of an inhaled partial dose is based on the aerosol flow rate at said point if the determined inhalation flow rate exceeds the aerosol flow rate at said point, and otherwise based on the determined momentary inhalation flow rate.

2. A method for measuring a dose of a drug inhaled by an experimental animal, the drug being supplied to the animal in the form of a flow of aerosol, characterised by the steps of (a) determining the momentary concentration of the drug in said flow of aerosol;

(b) at a frequency of at least 50 Hz, determining the momentary inhalation flow rate of the animal a plurality of times during each inhalation by the animal;

(c) calculating an inhaled partial dose for each determined momentary flow rate;

the total dose of the drug inhaled by the animal being obtained by summation of all inhaled partial doses.

3. A system for measuring a dose of a drug inhaled by an experimental animal, the drug being supplied, via a conduit system, to the animal in the form of a flow of aerosol from an aerosol generator, characterised by means for determining the momentary concentration of the drug in said flow or aerosol;

means for determining the momentary inhalation flow rate of the animal;

calculating means for calculating an inhaled partial dose for each determined inhalation flow rate as well as for adding up a plurality of inhaled Partial doses of obtaining the total dose inhaled by the animal, characterised by an air inlet for supplying additional air to the conduit system and an air outlet from the conduit system, said air inlet and said air outlet being located down-stream from the means for determining the concentration.

4. A system according to claim 3, characterised in that the means for determining the inhalation flow rate are arranged to determine the air flow rate in the air outlet.

5. A system according to claim 3, characterised in that the air outlet is connected to the conduit system upstream of the means for determining the momentary concentration of the drug in said flow of aerosol.

6. A method for administering a predetermined dose of a drug to an experimental animal, comprising the steps of aerosolishing the drug and supplying it in the form of a flow of aerosol to the animal, characterised by the further steps of (a) determining the momentary concentration of the drug in said flow of aerosol;

(b) determining the momentary inhalation flow rate of the animal a plurality of times during each inhalation by the animal;

(c) calculating an inhaled partial dose for each determined momentary flow rate;

(d) successively cumulating the calculated inhaled partial doses to a cumulated inhaled dose;

(e) interrupting the generation of aerosol when the cumulated inhaled dose is approximately equal to the predetermined dose, wherein the aerosol flow rate at the point where the momentary concentration of the drug is determined, is known or is determined, characterised in that the calculation of an inhaled partial dose is based on the aerosol flow rate at said point if the determined inhalation flow rate exceeds the aerosol flow rate at said point, and otherwise based on the determined momentary inhalation flow rate.

7. A method for administering a predetermined dose of a drug to an experimental animal, comprising the steps of aerosolishing the drug and supplying it in the form of a flow of aerosol to the animal, characterised by the further steps of (a) determining the momentary concentration of the drug in said flow of aerosol;

(b) at a frequency of at least 50 Hz, determining the momentary inhalation flow rate of the animal a plurality of times during each inhalation by the animal;

(c) calculating an inhaled partial dose for each determined momentary flow rate;

(d) successively cumulating the calculated inhaled partial doses to a cumulated inhaled dose;

(e) interrupting the generation of aerosol when the cumulated inhaled dose is approximately equal to the predetermined dose.

8. A system for administering a predetermined dose of a drug to an experimental animal in the form of a flow of aerosol, comprising an aerosol generator which is connected to a conduit system for supplying the aerosol generated by the aerosol generator to the experimental animal, characterised by means for determining the momentary concentration of the drug in said flow of aerosol;

means for determining the momentary inhalation flow rate of the animal;

calculating means for calculating an inhaled partial dose for each determined momentary inhalation flow rate as well as for successively cumulating the calculated inhaled partial doses to a cumulated inhaled dose;

comparing means for comparing the cumulated inhaled dose with the predetermined dose; and means for turning off the aerosol generator when the cumulated inhaled dose is approximately equal to the predetermined dose;

characterised by an air inlet for supplying additional air to the conduit system and an air outlet from the conduit system, said air inlet and said air outlet being located downstream from the means for determining the concentration.

* * * * *